(12) United States Patent
Laster et al.

(10) Patent No.: US 6,463,933 B1
(45) Date of Patent: Oct. 15, 2002

(54) BONE MARROW AS A SITE FOR TRANSPLANTATION

(76) Inventors: Morris Laster, Segal Street 40, Jerusalem, 97289 (IL); Lindsay Rosenwald, 441 W. End Ave., New York, NY (US) 10024

(*) Notice: Subject to any disclaimer, the term of this patent is extended or adjusted under 35 U.S.C. 154(b) by 0 days.

(21) Appl. No.: 09/381,720
(22) PCT Filed: Mar. 25, 1998
(86) PCT No.: PCT/US98/05829
§ 371 (c)(1), (2), (4) Date: Feb. 7, 2000
(87) PCT Pub. No.: WO98/42270
PCT Pub. Date: Oct. 1, 1998

Related U.S. Application Data
(60) Provisional application No. 60/041,370, filed on Mar. 25, 1997.

(51) Int. Cl.⁷ .............................................. A61B 19/00
(52) U.S. Cl. ........................................................ 128/898
(58) Field of Search ......................... 128/898; 435/325, 435/320.1, 375, 455; 424/93.1, 93.7, 93.21, 422, 426

(56) References Cited

U.S. PATENT DOCUMENTS

| | | |
|---|---|---|
| 4,486,188 A | 12/1984 | Altshuler et al. |
| 4,859,584 A | 8/1989 | Horan et al. |
| 5,186,931 A | 2/1993 | Kishimoto et al. |
| 5,399,346 A | 3/1995 | Anderson et al. |
| 5,461,034 A | 10/1995 | Rodan et al. |
| 5,489,306 A | 2/1996 | Gorski |
| 5,503,558 A | 4/1996 | Clokie |
| 5,514,364 A | 5/1996 | Ildstad |
| 5,589,466 A | 12/1996 | Felgner et al. |

FOREIGN PATENT DOCUMENTS

WO   WO90/11092   10/1990

OTHER PUBLICATIONS

Ahmed et al., 1994, "Extraction and quantitation of neuropeptides in bone by radioimmunoassay", Regulatory Peptides 51:179–188.

Bachar–Lustig et al., 1995, "Megadose of T cell–depleted bone marrow overcomes MHC barriers in sublethally irradiated mice", Nature Med. 1:1268–1273.

Bracy et al., 1998, "Inhibition of xenoreactive natural antibody production by retroviral gene therapy", Science 281:1845–1847.

Brickman et al., 1987, "A comparative study of intraosseous versus peripheral intravenous infusion of diazepam and phenobarbital in dogs", Ann. Emerg. Med. 16:1141–1144.

Cameron et al., 1989, "A comparative study of peripheral to central circulation delivery times between intraosseous and intravenous injection using a radionuclide technique in normovolemic and hypovolemic canines", J. Emergency Med. 7:123–127.

Doherty, 1995, "Anatomical environment as a determinant in viral immunity", J. Immunol. 155:1023–1027.

Evans et al., 1995, "Intraosseous infusion—a technique available for intravascular administration of drugs and fluids in the child with burns", Burns 21:552–553.

Fonkalsrud, 1968, "Evaluation of the bone marrow space as an immunologically–privileged site for allogeneic skin grafting", Surgery, Gynecology and Obstetrics, pp. 71–75.

(List continued on next page.)

Primary Examiner—David J. Isabella
(74) Attorney, Agent, or Firm—Pennie & Edmonds LLP

(57) ABSTRACT

The invention relates to a process for culturing cells by introducing the cells into the bone or bone marrow of a mammal. The invention also relates to a method for delivering a biologically active substance, including a nucleic acid, vector, protein or pharmaceutical composition to a mammal by introducing the substance into the bone or bone marrow.

2 Claims, 8 Drawing Sheets

OTHER PUBLICATIONS

Fonkalsrud, 1969, "Thyroid allografts implanted in the marrow space of rabbits. A functional and morphological evaluation", Arch. Surg. 98:738–741.

Hartley et al., 1993, "Elimination of self–reactive B lymphocytes proceeds in two stages: arrested development and cell death", Cell 72:325–335.

Hirsch et al, 1999, "Depressed T–cell interferon–Y responses in pulmonary tuberculosis: analysis of underlying mechanisms and modulation with therapy", J. Infect. Dis. 180:2069–2073.

Hopkins, 1990, "Pediatric intraosseous infusion", J. Louisiana State Med. Soc. 142:31–32.

Horowitz and Friedlaender, 1987, "Immunologic aspects of bone transplantation. A rationale for future studies", Orthop. Clin. North Am. 18:227–233.

Iwama et al., 1994, "Clavicular approach to intraosseous infusion in adults", Fukushima J. Med. Sci. 40:1–8.

Neish et al., 1988, "Intraosseous infusion of hypertonic glucose and dopamine", Am. J. Dis. Children 142:878–880.

Orlowski et al. 1989, "The bone marrow as a source of laboratory studies", Ann. Emerg. Med. 18:1348–1351.

Paramithiotis and Cooper, 1997, "Memory B lymphocytes migrate to bone marrow in humans", Proc. Natl. Acad. Sci. USA 94:208–212.

Piotrowski and Croy, 1996, "Maternal cells are widely distributed in murine fetuses in utero", Biol. Reprod. 54:1103–1110.

Posselt et al, 1991"Intrathymic islet transplantation in the spontaneously diabetic BB rat", Ann Surg. 214:363–373.

Ricordi (ed.), 1992, *Pancreatic Islet Cell Transplantation*, R.G. Landes Co., Austin, TX, pp. 177–237 and 317–319.

Rybka et al., 1995, "Hematopoietic progenitor cell content of vertebral body marrow used for combined solid organ and bone marrow transplanation", Transplantation 59:871–874.

Seyedin et al., 1986, "Cartilage–inducing factor–A. Apparent identity to transforming growth factor–$\beta$", J. Biol. Chem 261:5693–5695.

Streilein, 1995, "Unraveling immune privilege", Science 270:1158–1159.

Tafuri et al., 1995, "T cell awareness of paternal alloantigens during pregnancy", Science 270:630–633.

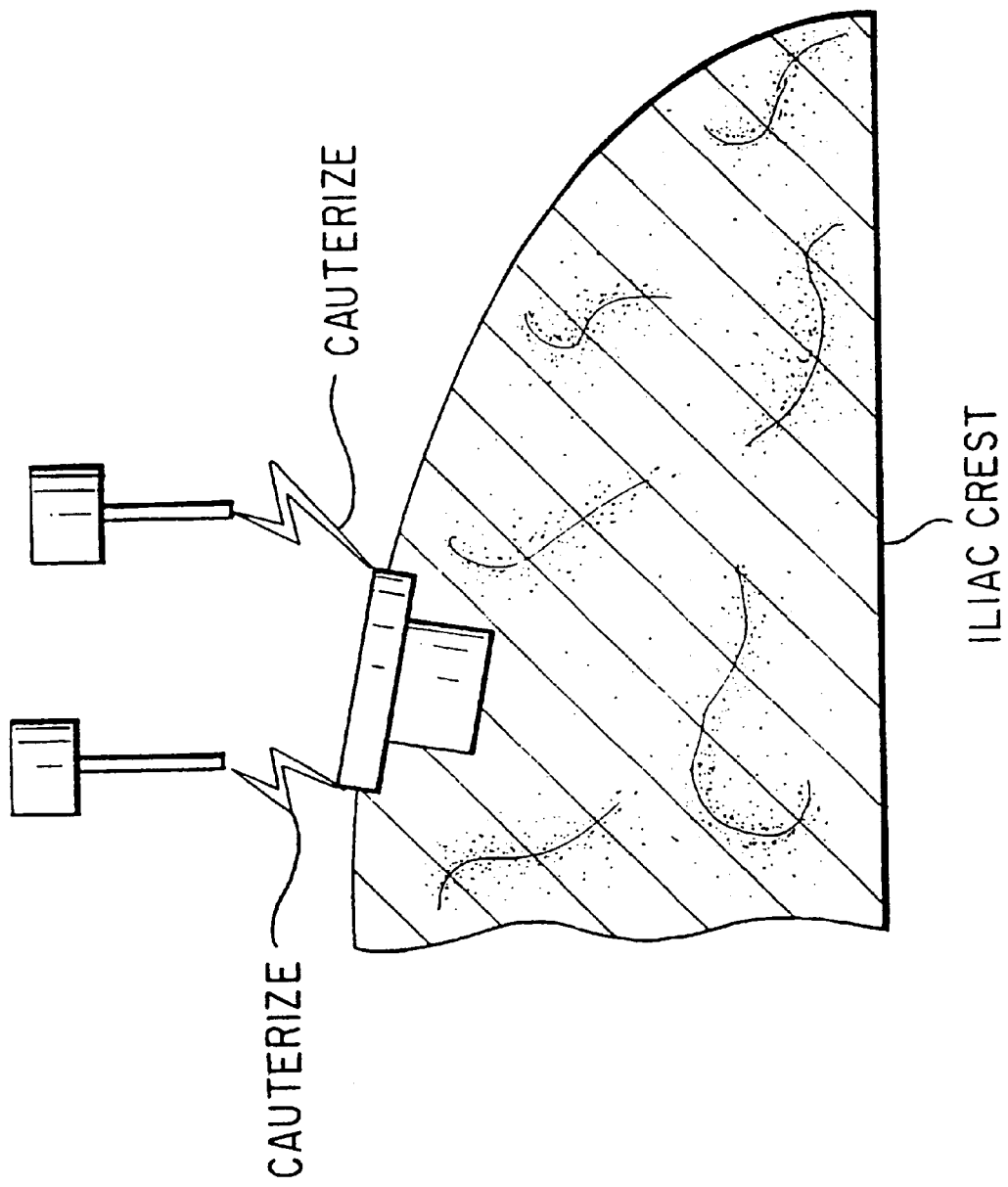

BONE MARROW AS A SITE FOR TRANSPLANTATION

This application is a 371 of PCT/US/98/05829 filed Mar. 25, 1998; which claims benefit to Provisional Application No. 60/041,370 filed Mar. 25, 1997.

BACKGROUND OF THE INVENTION

1. Field of the Invention

The present invention relates to a process for culturing cells by introducing the cells into the bone or bone marrow of a mammal. The invention also relates to a method for delivering a biologically active substance to a mammal by introducing the substance into the bone or bone marrow.

2. Discussion of the Background

The bone marrow (BM) is an organ present between the cortical walls of bone. In infancy and childhood, the bone marrow of the entire body is involved in hematopoiesis. In the adult, hematopoiesis is limited to axial skeleton (skull, sternum/ribs, vertebral bodies, iliac crests).

The BM provides access to the circulatory system, and additionally to hematopoietic stem cells and stromal cells. In the past, intra-osseous bone infusions were used as a method for pediatric resuscitation when an IV was not easily accessible. This approach was abandoned with the advent of improved venous access devices. Later, the technique underwent a revival in pediatric trauma and burn victims [(Evans et al, *Burns* 21(7):552–3 (1995); Hopkins et al, *Jrnl of the Louisiana State Medical Society* 142(3):31–2, 1990)].

That the bone marrow may be an immunoprivileged site is supported by the literature. Paramithiotis and Cooper showed that antigen-experienced B lymphocytes do not secrete Ig spontaneously when removed from the bone marrow, even though this occurs when these lymphocytes are removed from other locations. Yokichi et al disclosed the decreased responsiveness of bone marrow macrophages versus peripheral macrophages to LPS stimulation. This includes a decreased bone marrow macrophage response even in the face of pre-sensitization with LPS. Hirsch et al describes the immunosuppressive effects of TGFβ in the T cell response to TB. Because TGFβ is present in large amounts in the bone and thus the bone marrow. These reports are consistent with a theory that the bone marrow micro-environment is immunosuppressive.

Other studies have shown the utility of intra-osseous infusions for withdrawing laboratory samples [(Orlowski et al, *Annals of Emergency Medicine* 18(12):1348–51 (1989)] and for infusion of pharmacologically active compounds [(Cameron et al, *Jrnl of Emergency Medicine* 7(2):123–7 (1989); Neish et al, *Am J of Diseases of Children* 142(8):878–80 (1988); Brickman et al, *Annals of Emergency Medicine*, 16(10):1141–4 (1987)]. One such study measured the flow rates in a clavicular intra-osseous infusion—and found it to be statistically similar to sub-clavian vein flow, while the iliac crest was found to have a flow twice that of the sub-clavian vein [(Iwama et al, *Jrnl of Medical Science* 40(1):1–8 (1994)].

Sites in the body which are immunologically privileged can be utilized for the introduction of materials foreign to the host. Immune privilege may stem from either immune suppression, immune deviation, or active tolerance induction. Features characteristic of immune privileged sites include the presence of a blood tissue barrier, cytokines such as TGF-β, neuropeptides, the presence of antigen presenting cells which actively induce tolerance, and other factors [(Streilin, *Science* 270(5239)1158–9 (1995)].

Immune privileged sites have developed in specific compartments of the body in which immune stimulation might be harmful to the host, due to the presence of tissue which may be seen as foreign. These sites are then compartmentalized in some way so as to create a micro-environment conducive to immune suppression and active immune tolerance.

An example of an immune privileged site is the pregnant uterus. The placenta and fetus represent foreign tissue to the mother, yet these antigens are under normal circumstances not rejected. The mother and fetus interconnect via sinusoids present between the placenta and uterus. During pregnancy, there are fetal blood cells present within the maternal circulatory system. These cells and fetus are not rejected so long as the compartmentalization of this foreign tissue and it's interface with the non-immune privilege host, is not compromised. So long as the compartments remain whole, the microenvironment is conducive for immune suppression via local growth factors such as TGF-β, presence of Fas-ligand, and ACAID (anterior chamber associated immune deviation).

Once the compartment is breached, as occurs during the separation of the placenta from the uterus, the status of immune privilege is breached, and the mother can mount an immune response against the fetus, which is the situation of an Rh negative mother with an Rh positive fetus. Throughout the initial pregnancy with and Rh positive fetus, there is no immune response to the Rh antigen. Once the compartment is breached following delivery, if Rhogam is not administered, the mother will develop a permanent response to Rh antigen, which may result in an attack on the next Rh positive fetus [(Tafuri et al, *Science* 270:630 (1995)].

As noted above, an immune privileged site may exist as a discrete "microenvironment." The microenvironment in which an antigen exists or is present determines the host response to it. The phenotype of immunity is modulated by the range of environments that lymphocytes experience as they pass through, or lodge in for a time [Doherty, *J. Immunol.* 155(3):1023–7 (1995)].

To date, the use of bone marrow was mainly limited to the use of BM derived cells for use in hematopoietic transplantation. However, in 1968, Fonkalsrud described the possibility for using the bone marrow space as an immunologically-privileged site for allogeneic skin grafting (*Surgery, Gynecology & Obstetrics*, pp. 71–75). In 1969, Fonkalsrud again described the possibility of using the marrow space for implants, this time for thyroid allografts (Arch. Surg. Vol 98, pp. 738–741. However, there have been no reports of transplantation into the bone marrow of other types of cells, such as hepatocytes and pancreatic islet cells or for the use of the BM space for the delivery of peptides, drugs, genes nor for the use of the space for the culture of cells for use in transplantation such as hepatocytes, nervous, cardiac or other useful tissue. Ricordi (*Pancreatic Islet Cell Transplantation*, p. 317–319 (1992), which is incorporated herein by reference in its entirety) has shown that non-immunoisolated rat-to-mouse islet xenografts show poor survival, however, islets have not been transplanted into bone marrow.

In view of the aforementioned lack of utilization of the bone marrow for surgical intervention, there exists a need in the art for such a method.

SUMMARY OF THE INVENTION

Accordingly, one object of this invention is to provide a method for culturing cells comprising transplanting the cells into the bone marrow of a mammal.

Another object of the invention is to provide a method for transplanting cells into a mammal comprising delivering the cells into the bone marrow of a mammal.

Still another object of the invention is to provide a method for delivering a functional gene into a mammal comprising delivering a cell transformed with a vector containing the gene into the bone marrow of a mammal.

Yet another object of the invention is to provide a method for delivering a biologically active protein or peptide to a mammal, comprising delivering a cell transformed with a vector which expresses a gene encoding the protein or peptide into the bone marrow of a mammal.

Another object of the invention is to provide a method for delivering a biologically active protein or peptide to a mammal, comprising delivering a DNA encoding the protein or peptide to the bone marrow of a mammal.

A further object of the invention is to provide a method for delivering a biologically active protein or peptide to a mammal comprising delivering said protein or peptide in a suitable carrier to the bone marrow of a mammal.

A further object of the invention is to provide a method for delivering a pharmaceutical to a mammal comprising delivering the pharmaceutical in a suitable carrier to the bone marrow of a mammal.

Another object of the invention is to provide a method for performing bone marrow transplants.

Still another object of the invention is to provide a method for inducing tolerance to an antigen in a patient prior to treatment.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 3 is a schematic demonstrating a cell/organ/device transplant procedure in accordance with the present invention.

FIG. 3A demonstrates an initial step in the transplant procedure, cauterization.

DETAILED DESCRIPTION

Figure 1:
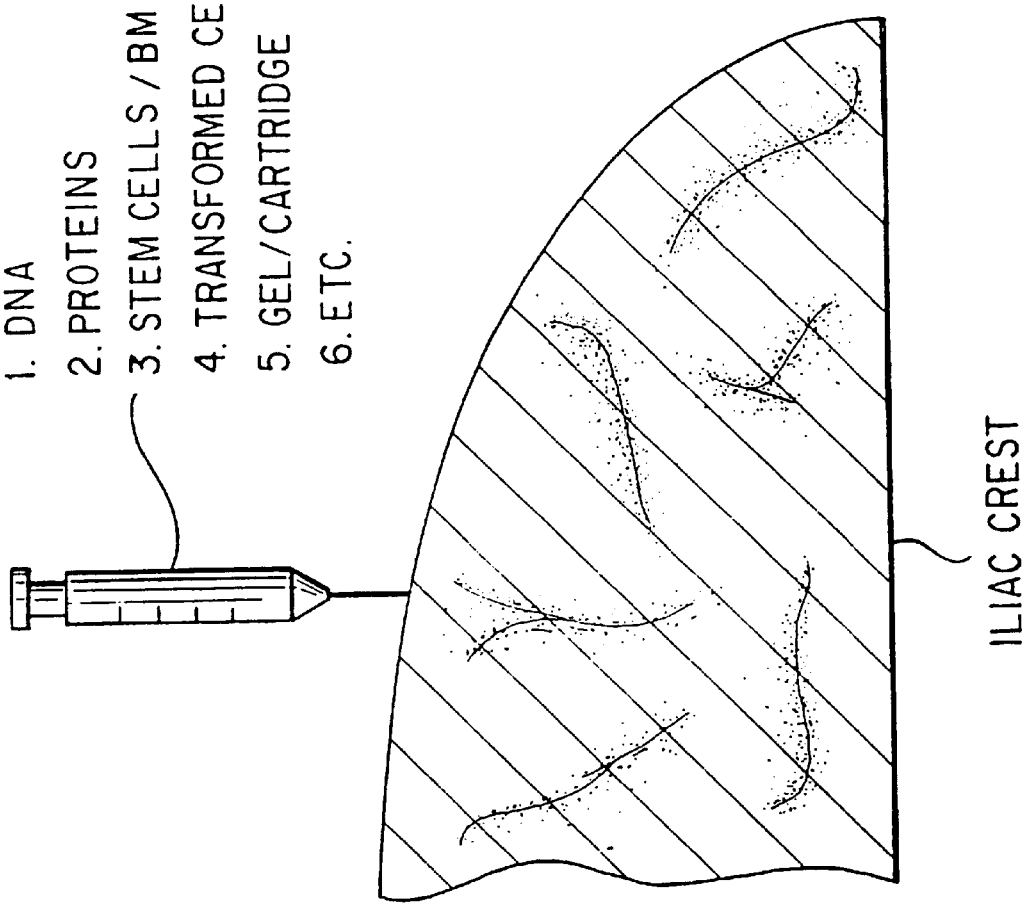
FIG. 1 is a schematic which demonstrates the various compositions and delivery systems which can be used in accordance with the present invention for direct bone marrow injection.
Figure 2:
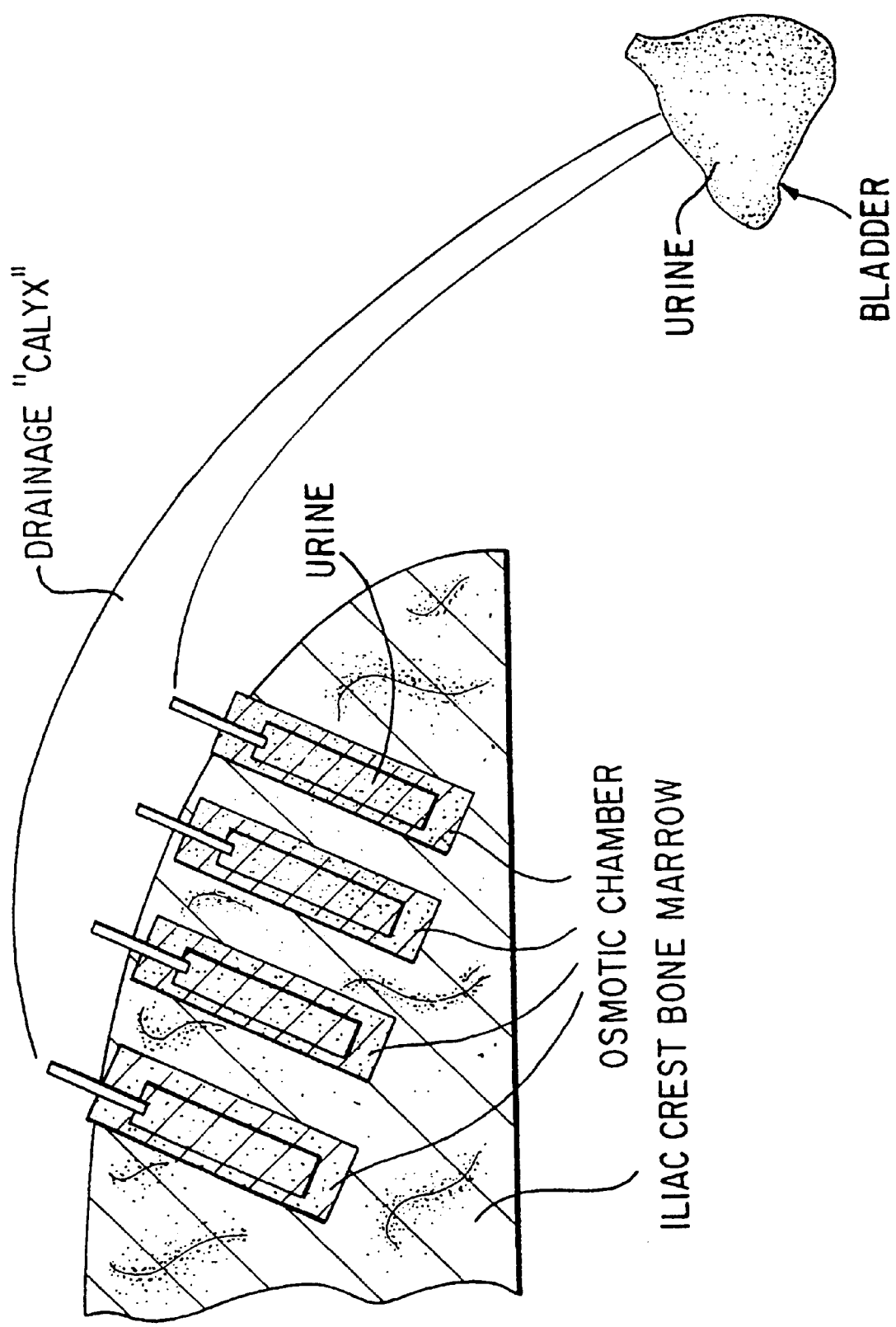
FIG. 2 is a schematic which demonstrates how an artificial intra-osseous dialysis device would be used in accordance with the present invention.
Figure 3B:
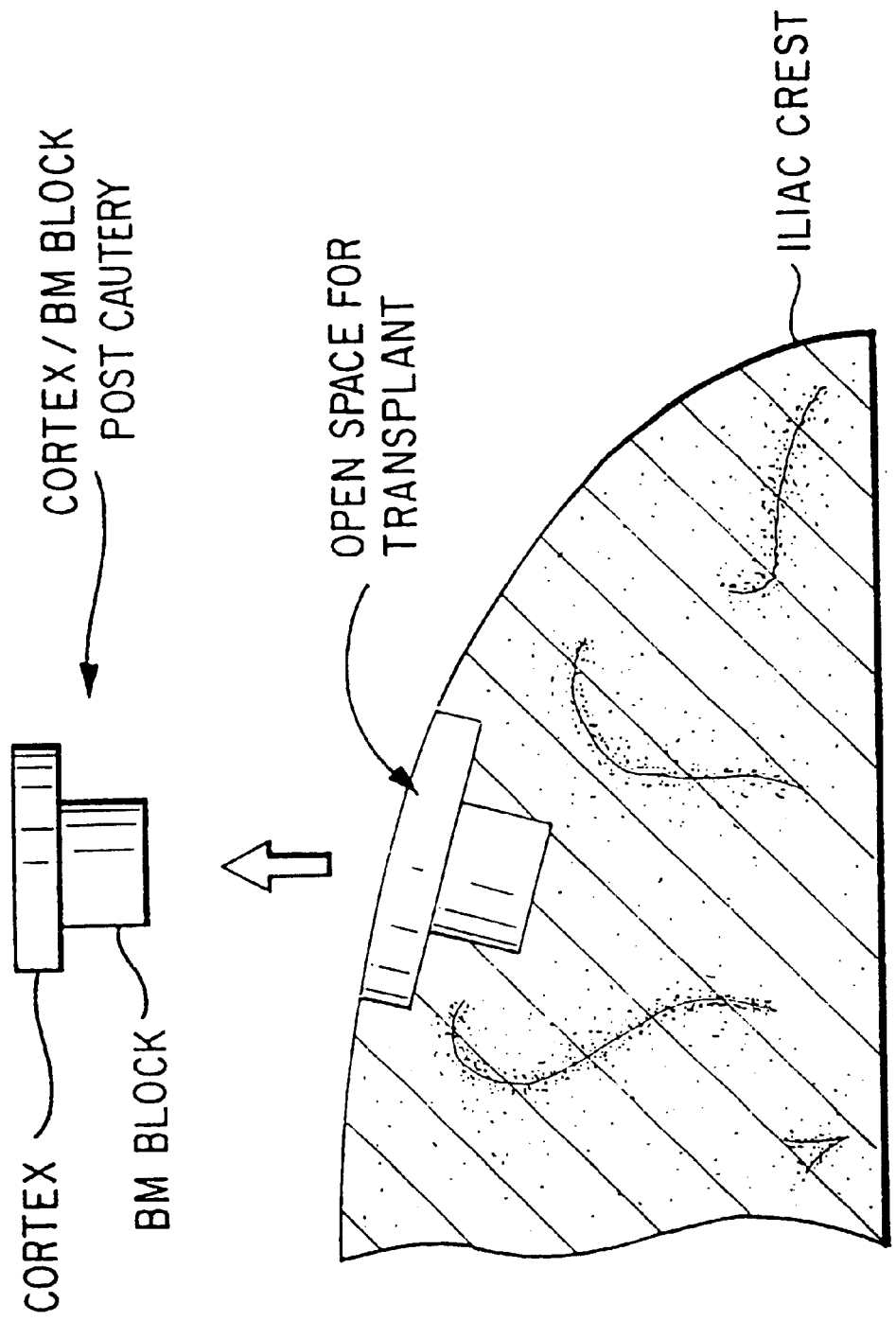
FIG. 3B demonstrates the removal of the cortex/bone marrow block, leaving an open space in which to place the transplanted material.
Figure 3C:
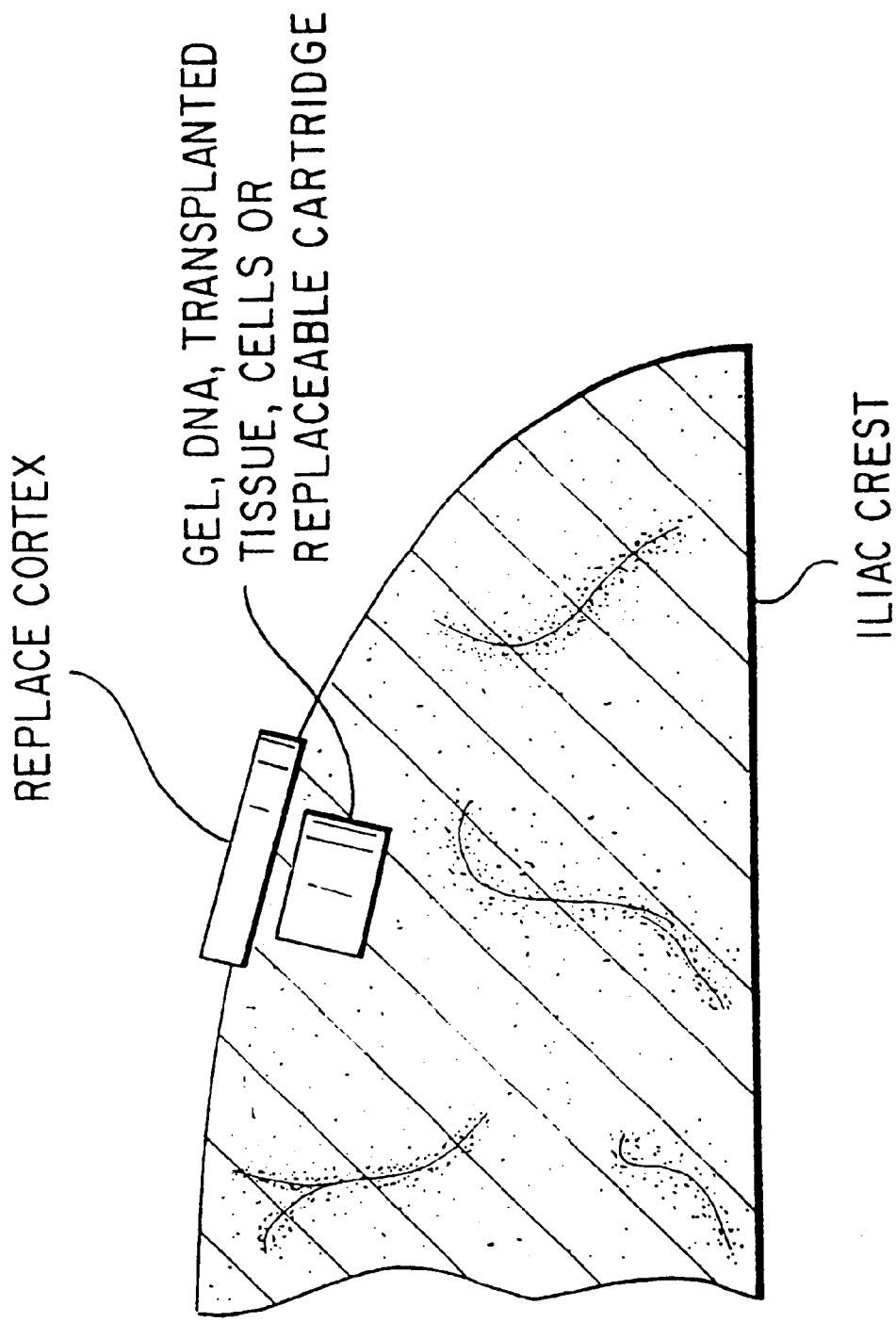
FIG. 3C demonstrates a final step of the bone marrow transplantation, wherein the transplanted material is inserted into the open space, and the cortex is replaced.

The present invention recognizes that the bone marrow is a suitable site for delivering foreign cells, genes, proteins and pharmaceuticals. Firstly, because the bone marrow is a natural arterial-venous graft, it provides easy access to the circulatory system with minimal procedure. Moreover the bone marrow is particularly well suited to such delivery systems, because it is an immune privileged site, and thus delivery to the bone marrow eliminates a host immune response to the transplanted material.

With respect to the bone marrow being a natural arterial-venous graft, there exists a "dual system" of circulation in bone, i.e., the outflowing nutrient-marrow and the inflowing periosteal-Haversian. This dual system provides for the necessities of homeostasis. While the nutrient artery is mainly responsible for erythropoiesis, the periosteal-cortical circulation is more closely related with the osteogenic side of homeostasis [Trueta, *Studies of the Development and Decay of the Human Frame,* William Heinemann Medical Books, Ltd, London, (1968)]. It is this dual circulation which provides the circulatory basis for the compartmentalization of the bone marrow from the remainder of the body.

The bone marrow is used as circulatory access in pediatric trauma and burns. Moreover, the bone marrow can be used to withdraw laboratory samples, and has a flow rate greater than that of a central vein.

The bone marrow is compartmentalized to create a micro environment conducive to immune suppression and active immune tolerance. The presence of cytokines, antigen-presenting cells which actively induce tolerance and other factors are in part responsible for creating this micro-environment. The immune privilege of the bone marrow is thus dependent on the separation of the periosteal/cortical circulation from the bone marrow. A breach in the integrity of this separation may result in a loss of immune privilege. However, because surgical procedures allow one to "sterilely" arrive at the bone marrow while preserving the integrity of the compartment, the bone marrow can be used as a site for cellular transplantation.

Previous experiments performed on bio-hybrid pancreas or liver, require vascular procedures to ensure access to the circulatory system. Moreover, previous micro-encapsulation experiments [Ricordi, *Pancreatic Islet Cell Transplantation,* pp. 177–237, R. G. Landes Col., Austin, Tex. (1992)] have shown that capsules transplanted into the peritoneum are eventually suffocated by fibroblast cell overgrowth. Due to the nature of blood circulation in the marrow, implantation of such capsules into the bone marrow solves this problem as well. Since the bone marrow functions as a naturally occurring arterio-venous (A-V) graft, implantation of cells or bio-hybrid systems into the bone marrow results in simple access to the circulatory system.

The micro-environment of the bone marrow entails many if not all of the features associated with other immune privileged sites. One of the characteristics of an immune privileged site is the existence of a barrier system which exists in bone as a result of the dual circulation of bone described by Trueta, supra. Evidence that the bone marrow is an immune privileged site includes the existence of molecules in the bone marrow which have been associated with such immune privilege. In particular, bone matrix contains a large amount of TGF-β [Seydin et al, *J. Biol. Chem.* 261:5693–5695 (1986)]. Additionally, neuropeptides such as Substance P, VIP and CGRP are all present in bone [Kreicsbergs et al, *Regulatory Peptides* 51(3):179–188 (1994)].

In addition, CD34+ cells can express Fas-L when properly stimulated. The deactivation of immune cells in the bone marrow may be a direct result of Fas-ligand. Moreover, hematopoietic stem cells present in large quantities in bone marrow, can constitutively express Fas-ligand under specific circumstances.

Additional evidence in support of the bone marrow being an immune privileged site includes tolerance studies in which dendritic cells were extracted from vertebral body bone marrow [Starzl et al, *Transplantation* 59(6):871–4 (1995)]. These cells were termed facilitator cells and were instrumental in the establishment of BMT chimerism. It has also been shown that self-reactive B-cells are de-activated within the bone marrow [Goodnow et al, *Cell* 73(2):325–35 (1993)]. Bone or the cells found in bone may induce an inhibitory effect on specific alloreactivity [Friedlander et al, *The Orthopedic Clinics of North America* 18(2):227–33 (1987)]. Thus, the bone marrow is an ideal site for cellular transplantation.

The use of osseous and osteochondral allografts, and the immunological aspects thereof are described in Horowitz and Friedlander et al (1987), which is incorporated herein by reference in its entirety.

As used hereinafter, the term "material to be implanted" is meant to include cells, tissues and other compositions and carriers for an exogenously introduced gene, protein or pharmaceutical composition, wherein the compositions and carriers are intended to provide treatment to the host. The present invention allows for the implantation of various cells, devices, genetic material and pharmaceuticals which require access to the circulatory system to be effective.

Any host organism may be used, with the proviso that the organism contains bone and bone marrow. The anatomy and circulation of bone is described in Trueta, *Studies of the Development and Decay of the Human Frame,* William Heinemann Medical Books, Ltd, London, (1968) which is incorporated herein by reference in its entirety. Thus, the organism must be a vertebrate, preferably a mammal. The host may be of any age, including any gestational age.

Any type of cell or tissue can be transplanted into the bone (i.e., intra-osseous) or bone marrow using the method of the present invention. The cellular material may be an autograft or an allograft. In a preferred embodiment, the cellular material is liver or pancreatic islet cells. Transplantation of islet cells is described in Posselt et al, *Ann. Surg.* 214:363–373 (1991), which is incorporated herein by reference in its entirety.

In another preferred embodiment, the method of the present invention is used to provide a bone marrow transplant. Thus, in this case, the cellular material is obtained from the bone marrow of a donor patient.

It is preferable to obtain the cellular material either from the host or from a donor related by blood, particularly a parent, sibling or child of the host. Where the cellular material is an allograft, the donor may be pretreated with a pharmaceutical composition, cytokine or lymphokine which will reduce rejection of the implanted material. In addition, the host may be treated during the incubation period of the transplanted cells in the bone marrow.

In addition, patients may be pre-tolerized with antigens prior to transplantation for improved outcome. Patients may likewise be tolerized to allergans via IO injection. Direct BM injection to the IO space may reduce GvHD and HvGD.

The method of the present invention is thus useful for cell therapy. Cells may be delivered directly into the bone marrow to reconstitute or replenish areas where cell numbers or activity is diminished. Preferred cells for implantation into the bone marrow may include encapsulated and non-encapsulated cells. Examples of such cells include hepatocytes or pancreatic islet cells. A particularly preferred implantation site is the iliac crest (IC).

The cells which are implanted may be normal or genetically engineered cells, as described further below. In addition to providing cells in tissue form or suspension, the cells may be implanted in the form of impregnated gels or as hollow fiber cell implants.

Another aspect of the cell transplantation of the present invention is assisting in bone marrow transplantation (BMT) engraftment. Recent evidence has shown that increasing the numbers of stem cells can assist in BMT engraftment [Reisner et al, *Nature Medicine* 1(12):1268–1273 (1995)]. Direct injection of BM cells into the IO space may result in a functional increase in the numbers of stem cells engrafting. Factors present in the bone marrow which assist BM engraftment include the three dimensional matrix of the BM and the production of proliferative cytokines by stromal cells.

In addition to providing a suitable culture environment for cells and tissues, the bone marrow provides an ideal location for the administration of exogenous genes, proteins and pharmaceutical compositions. Because the bone marrow is an immune privileged site, an immune response to the material which is administered, particularly proteins (including antibodies) and pharmaceutical compositions, is minimal.

The method of the present invention can likewise be used for implanting devices in the bone marrow. Particularly preferred devices for implantation into the bone marrow include drug release devices, or dialytic devices. Such dialytic devices, once implanted in the bone marrow, can perform intra-osseous (IO) dialysis (and subsequently drain into the bladder via tubing).

A particularly preferred use of the present invention is for gene therapy. Genetic material may be introduced into the bone marrow in the form of transformed cells or naked DNA. Naked DNA injection has been shown to be an effective method of gene transduction [Montgomery et al, *Current Opinion in Biotechnology* 5(5):505–510 (1994)]. Because stem cells are present in their greatest concentrations in the BM, direct IO injection allows direct access to these target cells (bone marrow stem cells or stromal cells). A preferred method of the present invention is one in which a small dose chemotherapy or radiation therapy is given, and the genes are introduced during the replication phase. This method increases the incorporation of the genetic material into the target cells.

A particularly preferred target cell in the bone marrow is the stromal cell. BM stromal cells are secretary factories with direct access to the circulatory system, and are thus attractive targets for gene therapy [Clark et al, *Jrnl of Immunology,* 155(3):1023–7 (1995)].

As mentioned above, the present method may be used to administer a therapeutic substance to the host. The bone marrow is a particularly preferred site in this sense, because it contains stem cells which may be transformed by an exogenously administered nucleic acid, and may divide and differentiate to produce many daughter cells which additionally contain the exogenously administered nucleic acid.

Gene vectors may be injected into the BM for direct stem cell transduction or stromal cell transduction. Examples include retroviral vectors, liposomes, adenoviral vectors, DNA impregnated gels, and the like.

Thus, the material to be transplanted may include cells, both prokaryotic and eukaryotic, which are transformed with a vector containing a nucleic acid of interest.

The vector which is provided to the cells is preferably an expression vector, which expresses a protein which will have a therapeutic function in the host. The vector is chosen to contain a suitable promoter for expression in type of cell in which it is contained. The vector may be a plasmid vector or viral vector, preferably a viral vector which is not infectious in the host. However, the vector may also provide mRNA which can serve an antisense function, or may provide a nucleic acid or protein which can bind to other nucleic acids to provide a gene regulatory function.

Any protein may be administered by the present method. In particular, the therapeutic proteins which may be administered by the present method include angiogenin, epidermal growth factor, erythropoietin, fibroblast growth factor, granulocyte colony stimulatory factor, granulocyte-macrophage colony stimulating factor, heparin binding EGF like growth factor, hepatocyte growth factor, insulin, insulin-like growth factors, interleukins, interferons, leukemia inhibitory factor, macrophage colony stimulating factor, macrophage colony stimulating factor, monocyte chemotactic protein, monocyte chemotactic and activating factor, macrophage inflammatory protein, nerve growth factor, oncostatin, platelet-derived endothelial cell growth factor, platelet-derived growth factor, stem cell factor, transforming growth factor, tumor necrosis factor, vascular endothelial growth factor, and the like.

Alternatively, the material to be transplanted may include "naked" nucleic acids, proteins, and pharmaceuticals, i.e., nucleic acids, proteins and pharmaceuticals in a suitable medium or pharmaceutically acceptable carrier. The material to be transplanted may also include nucleic acids and proteins in a suitable carrier, which provides for a sustained release of the material. Such sustained release formulations are well known in the art, and may include capsules and tablets, liposomes, cartridges and gels. Methods for providing implants in bone are described in U.S. Pat. Nos. 5,503,558, 5,489,306 and 5,461,034, all of which are incorporated herein by reference in their entirety.

Suitable carriers may include sterile, pyrogen free water. The preparation of therapeutic compositions which contain polypeptides, or pharmaceuticals as active ingredients is well understood in the art. Typically, such compositions are liquid solutions or suspensions, however, solid forms suitable for solution in, or suspension in, liquid prior to transplantation can also be prepared. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, nucleic acid or pharmaceutical composition can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The compositions are administered in a therapeutically effective amount. The quantity to be administered depends on the subject to be treated and degree of treatment desired. Precise amounts of active ingredient required to be administered depend on the judgment of the practitioner and are peculiar to each individual. The carrier may additional comprise pharmaceuticals other than those which are considered to be the main therapeutic drug. In particular, antibiotics and/or other immune-suppressive substances may be included in the carrier.

The site of incubation of the material to be implanted may be any bone marrow in the body of the host. A preferred location is the iliac crest. The site of transplantation is preferably chosen for easy accessibility.

The host may optionally be pre-treated using chemotherapy or radiotherapy to further decrease any chance of immune response to the material to be transplanted and increase uptake in the replicative phase. Such immune-suppressive drugs and radiation regimens are well known in the art.

The method of delivery of the material to be transplanted may include any method which is capable of introducing the material into the bone or bone marrow. Preferably, the method is by injection, which is a relatively non-invasive procedure. The injection may be made directly into the bone or bone marrow, or may be made via catheter.

The site of administration of the material to be implanted may be any bone or bone marrow of the host. Preferably, the site is a hematopoietic intra-osseous (IO) site, preferably the iliac crest. Alternatively, the site may preferably include the skull, sternum, ribs and vertebra.

The incubation period for the material to be transplanted varies with the intended purpose. In other words, if the material to be transplanted is meant for cellular growth or expansion, the transplantation period may be days or weeks, up to a period extending for the life of the host. Alternatively, the material to be transplanted may cultured only until the desired level of cellular growth and expansion occurs. This "desired level" may be monitored by invasive procedures, including surgery, or by less invasive procedures which measure a level of some product or by-product of the transplanted cells or tissues, including the level of cytokine or lymphokine produced.

The incubation period for transplanted material which is meant to be administered for a therapeutic purpose, i.e., the nucleic acids, proteins and pharmaceutical compositions, may be only for a designated therapeutic duration, or may be for the life of the donor. In this case, the therapeutic regimen may include monitoring of the level of the nucleic acid, protein or pharmaceutical by standard diagnostic techniques including blood or urine tests, immunoassay including enzyme-linked immunosorbent assay (ELISA) or Western blot, or by detection of the nucleic acid by polymerase chain reaction, Southern or Northern blot.

The host may be a patient having a genetic abnormality, in which the method provides for the delivery of a normal gene to the host, or may provide for the delivery of a gene at considerably higher levels than normal. Such delivery may include "gene therapy," as described in U.S. Pat. No. 5,399,346 to French Anderson, and in U.S. Pat. No. 5,589, 466 to Felgner et al, corresponding to PCT publication WO 90/11092, all of which are incorporated herein in their entireties.

The host may also be a patient with an infectious disease, such as AIDS, or may be afflicted with a neurodegenerative disease such as Parkinson's Disease, Huntington's Disease or Alzheimer's Disease. In the case of AIDS, the transplanted material may include a therapeutic protein which down-regulates viral replication or gene expression, including interferon, or may be a pharmaceutical which inhibits replication or viral protein function, e.g., a protease inhibitor. In the case of a neurodegenerative disease, the transplanted material may include a neurotransmitter or neurotransmitter precursor which is diminished in the patient host, including dopamine, acetylcholine and the like. The host may be a diabetic in need of islet cell transplantation. Likewise, the host may be a patient in liver failure or fulminant hepatitis who may need a liver transplant or a bridge to liver transplantation. The present invention may also be used in the treatment of osteomyelitis and bone oncology.

Having generally described this invention, a further understanding can be obtained by reference to certain specific examples which are provided herein for purposes of illustration only and are not intended to be limiting unless otherwise specified.

EXAMPLES

Example 1
Analysis of Bone and Bone Marrow

Human bone is obtained from surgery. Bone fragment is washed with normal saline, and fixed with formalin. The tissue block is sliced and plated on slides. A tagged anti-CD95 ligand antibody is bound to slides for gross appraisal of the presence of Fas-ligand on bone or bone marrow.

Example 2
Preoperative Treatments

Anti-CD4 antibody is administered to the recipient to neutralize the natural antibody response. Alternatively, or in addition, TNF is administered to mobilize CD-95 on hematopoietic stem cells. Effective doses and suitable pharmacological carriers can be determined by those of ordinary skill in the art, in accordance with the description given above. In addition, or instead of the foregoing treatments, the recipient is treated with radiation or chemotherapy in doses which are known to those of skill in the art of cancer treatment.

Example 3
Surgical Procedure

The periosteum and apical cortex are divided with cautery/laser. The cancellous bone marrow is identified. A portion of the marrow is removed, and a graft of liver or other cellular material is transplanted in the resulting space. The cortex is then sealed over the transplant site, and the surgical site closed. Peri/post operative treatment may or may not require immuno-suppression.

Example 4
Injection into the Hematopoietic Marrow

Cellular material (autograft or allograft) is injected by the method of Example 3 or by direct needle injection into the hematopoietic marrow of a mammal with or without immuno-suppression.

Example 5
Injection of Bio-hybrid Structures into the Bone Marrow

Bio-hybrid structures such as those described above is inserted into the bone marrow as a transplant site by the method of Example 3 or by direct needle injection.

Example 6
Preparation of Cells for Introduction into the Bone Marrow Space

Rats were anesthetized with pentothal (in saline) IP at 40 mg/kg. The leg to be operated on was sterilized with betadine or alcohol. The tibia was exposed via incision made just below the knee, with gentle tissue retraction. Care was taken to ensure a dry operating field. 3–4 mm distal to the proximal tibia, a small hole was made with a dental drill and the bone marrow space was accessed. A cannula was then inserted approximately 1–1.5 cm into the bone marrow space of the tibia. Cells were injected via the cannula. Following the injection, the insertion site was sealed with bone wax.

Hepatocyte Harvesting

The liver was removed after washing with PBS via the portal vein. When the liver was white, collagenase 25 mg/10 ml was injected, and the tissue was then mechanically teased and incubated for 20 min at 37° C. The cells were then washed at 600 rpm for 3 minutes and suspended with F-12 medium.

Islet Cell Harvesting

The bile duct was cannulated, and collagenase P at a concentration of 4.2 mg/15 ml/rat was injected retrogradely into the pancreas. The pancreas was distended, placed in a plastic tube and incubated for 40 minutes in a 37° C. bath. 10 ml cold Hanks solution +1 g/l glucose was added, the mixture vortexed and centrifuged. The supernatant was removed and the cells were washed two times. The cells were then passed through a mesh filter and washed. To the pellet was added 10 ml Histopaque, the pellet was resuspended, and 10 ml Hanks basic salt solution added. The cells were centrifuged at 1500 rpm for 15 minutes. The band of cells was removed, 5 ml of Hanks solution was added, and then the cells were banded again. The cells were washed with RPMI-FCS two times with centrifugation at 500 rpm. The cells were then divided into two tubes, washed, resuspended and plated. One day after this preparation, the islets were examined and morphologically viable islets picked, based on relative size.

Streptozocin Induction of Diabetes

A Streptozocin preparation was made at a concentration of 60 mg/kg diluted with 2 ml of NaCl and a few drops of acetic acid. Injections were made intravenously or intraperitoneally. Animals were tested for hyperglycemia two days post-injection.

Example 7
Experiment 1

The objective of this experiment was to inject hepatocytes into the bone marrow space.

Rat 1 Syngeneic Hepatocyte injection.
Rat 2 HeLa (human cancer) cell injection Both rats were prepared as per the bone marrow transplant protocol outlined above. Rat 1 received an injection of 50–100 µl comprising 1.5–3×10 hepatocytes. Rat 2 Received an injection of 3×10 HeLa cells.

Rat 1 was sacrificed immediately post-operation. Rat 2 was sacrificed 3 days post-operation. Experimental tibias were fixed in formalin cut and stained.

For rat 1, hepatocytes were identified morphologically as being present interspersed throughout the BM space. For rat 2, anti-keratinocyte staining showed the presence of human HeLa cells in bone marrow space. No inflammation was seen around the xenogeneic cells.

The results obtained with both rat 1 and rat 2 demonstrate that cells had gained entry into the bone marrow space. The presence of human cells in the bone marrow of an immunocompetant animal 3 days post-op, without signs of inflammation demonstrates the efficacy of the present method.

Experiment 2

The objective of this experiment was to obtain syngeneic transplant. Sprague Dawley (SD) hepatocytes were introduced into the SD bone marrow space. Rats were sacrificed 3 days post-op and bones were prepared for histological exam.

Hepatocytes were identified morphologically throughout the bone marrow. Many hepatocytes were present in very obvious clusters with proliferation apparent in the various slices.

The results of this experiment demonstrates that the hepatocytes were properly placed in the BM. The BM environment appears to be conducive to survival and even proliferation. No apparent signs of inflammation or rejection were identified.

Experiment 3

The objective of this experiment was to provide syngeneic/allogeneic/xenogeneic transplants, and to compare entry through the cartilage versus the cortex for syngeneic transplants. Rat Group A was provided with SD hepatocytes into the SD bone marrow space in the right leg. Entry via the cartilage versus via the cortex was compared. In the left leg, SD Hepatocytes were introduced into the SD bone marrow space. For rat group B, both the right and left legs received mouse BA/C hepatocytes into the SD BM space. Rat Group C received human biopsy hepatocytes in the SD BM space. Injections comprised 2–3×10 cells in each leg. Group A was sacrificed at days 0, 3, 7 and 14. Groups B & C were sacrificed at 3 days.

Following sacrifice, bones were fixed, cut and stained. Counter staining with hepatocyte specific markers was performed on all groups.

For Group A, injection via the cartilage, as compared to entry via cortical injections, was a technically more difficult operation, while less bleeding and damage was obtained via the cortical injections. This resulted in more local inflamation at the site of entry in the cartilage experiments versus the cortical transplants.

Regardless of the method of entry, hepatocytes were identified morphologically on all sections, and were also identified via hepatocyte specific counter-staining using anti-albumin, pan-keratin AB and k167 on day 14.

For Group B, mouse hepatocytes were morphologically identified in rat BM on hematoxylin and eosin (H&E) staining. Hepatocyte specific counter-staining with k167, k19 and pan-keratin were positive on all sections. No apparent signs of inflammation, hyper-cellularity, infection or other immune response were noted.

For Group C, human hepatocytes were morphologically identified in rat BM on H&E staining. Hepatocyte specific counter-staining with k167, k19 and pan-keratin were positive on all sections. No apparent signs of inflammation, hyper-cellularity, infection or other immune response were noted.

Thus, the results from Group A show that the preferred mode of entry experimentally is via a cortical and not cartilaginous approach. The cartilaginous approach was apparently more traumatic and caused more bleeding. This however may not be the preferred embodiment in the human. Additionally, the presence of live syngeneic cells on day 14 shows the viability of the bone marrow as a site for hepatocyte transplantation. The cells are able to exist and survive without migration or other apparent adverse effect.

The results from Group B represent an allogeneic transplant in an immuno-competent animal without immunosuppression. The presence of hepatocytes confirmed by regular and counter-stain three days post-transplant demonstrates the efficacy of the present method. By three days post-transplant, one would expect to find some inflammatory response if it were going to occur, particularly because these cells are in constant contact with the blood.

The results from Group C represent a xenogeneic transplant in an immuno-competent animal without immunosuppression. The presence of hepatocytes confirmed by regular and counter-stain three days post-transplant demonstrates the efficacy of the present method. Again, by this time, one would expect to detect an inflammatory response if it were going to occur, particularly when because these xenogeneic cells are in constant contact with the blood.

The Group B and C experiments were repeated and the results were confirmed.

Example 8

Islet Transplantation in Diabetic Rats

To show that transplanted cells can function in the bone marrow environment as well as survive without immunosuppression, function of the cells was analyzed by analyzing the effect of transplantation of beta cells in streptozocin-induced diabetic rats.

Experiment 1

Syngeneic SD islet cells were transplanted into the SD bone marrow space, and glucose measurements were taken at various time points after transplantation.

Figure 4:
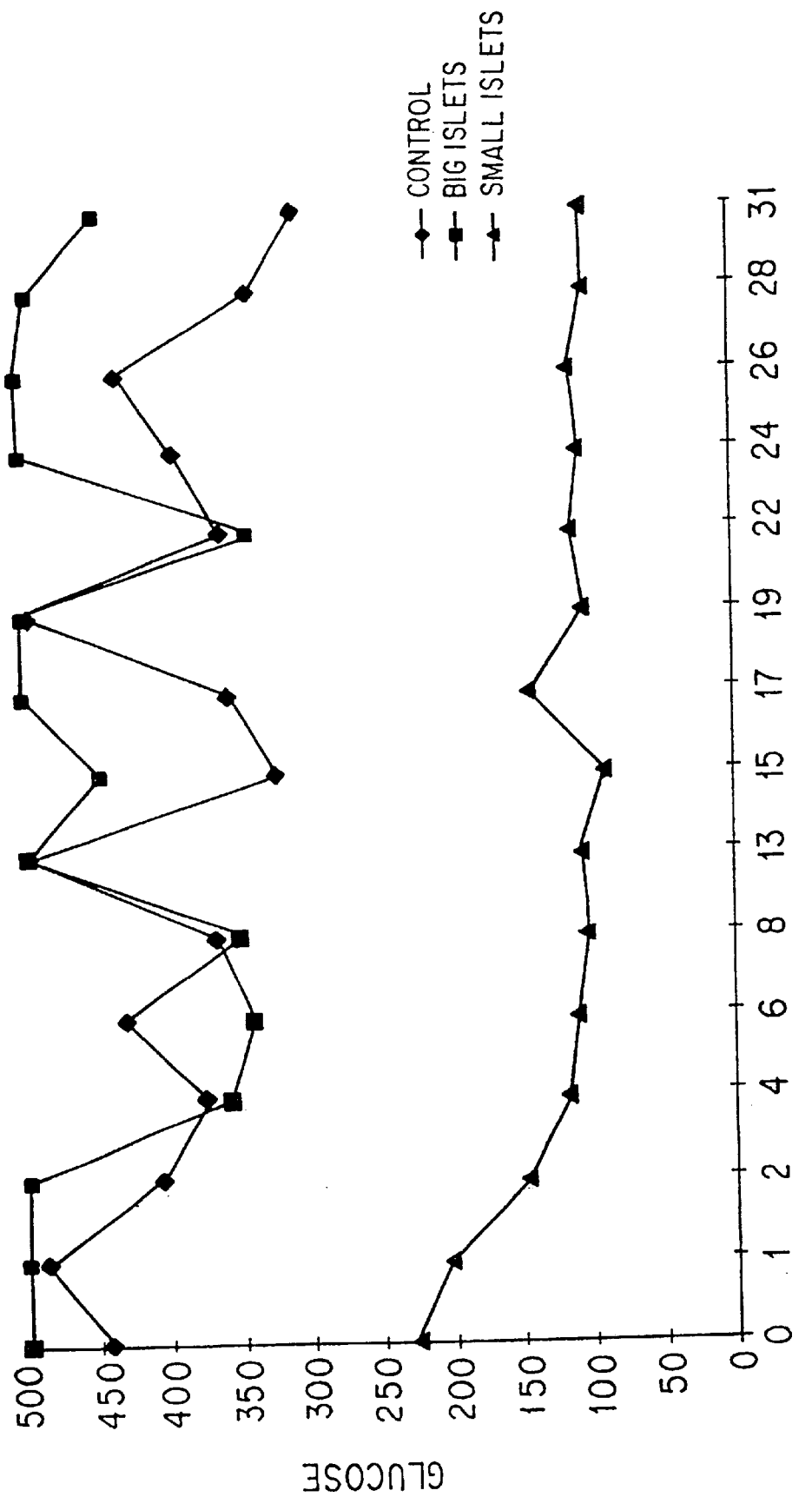
FIG. 4 shows the level of glucose through time in the presence of syngeneic SD-SD islet transplant.

Rat 1: 445—control
Rat 2: Hi—Transplanted with big islets
Rat 3: 228—Transplanted with small islets Results are shown in FIG. 4. In the syngeneic model, small islets were successfully transplanted. The large islets on morphological examination did not appear to function well. However, the experiment demonstrates that cells transplanted in the bone marrow can function and survive for at least 30 days. This proves that the BM space can be used as a site for the production of proteins that need to be secreted into the circulatory system, and is thus a viable site for both genetic and cellular transplantation.

Experiment 2

This experiment utilized an allogeneic transplant of Lewis rat islets into the Wistar rat BM space and SD islets into the Wistar rat BM space.

Five rats were prepared with streptozocin injection and four were transplanted, as follows:

| Rat 1 | Medium - control |
|---|---|
| Rat 2 | 90 Lewis Islets (donor 1) |
| Rat 3 | 90 SD Islets from prior experiment (cultured for 2 weeks) |
| Rat 4 | 140 Lewis Islets (donor 2) |
| Rat 5 | 140 Lewis Islets (donor 2) |

Figure 5:
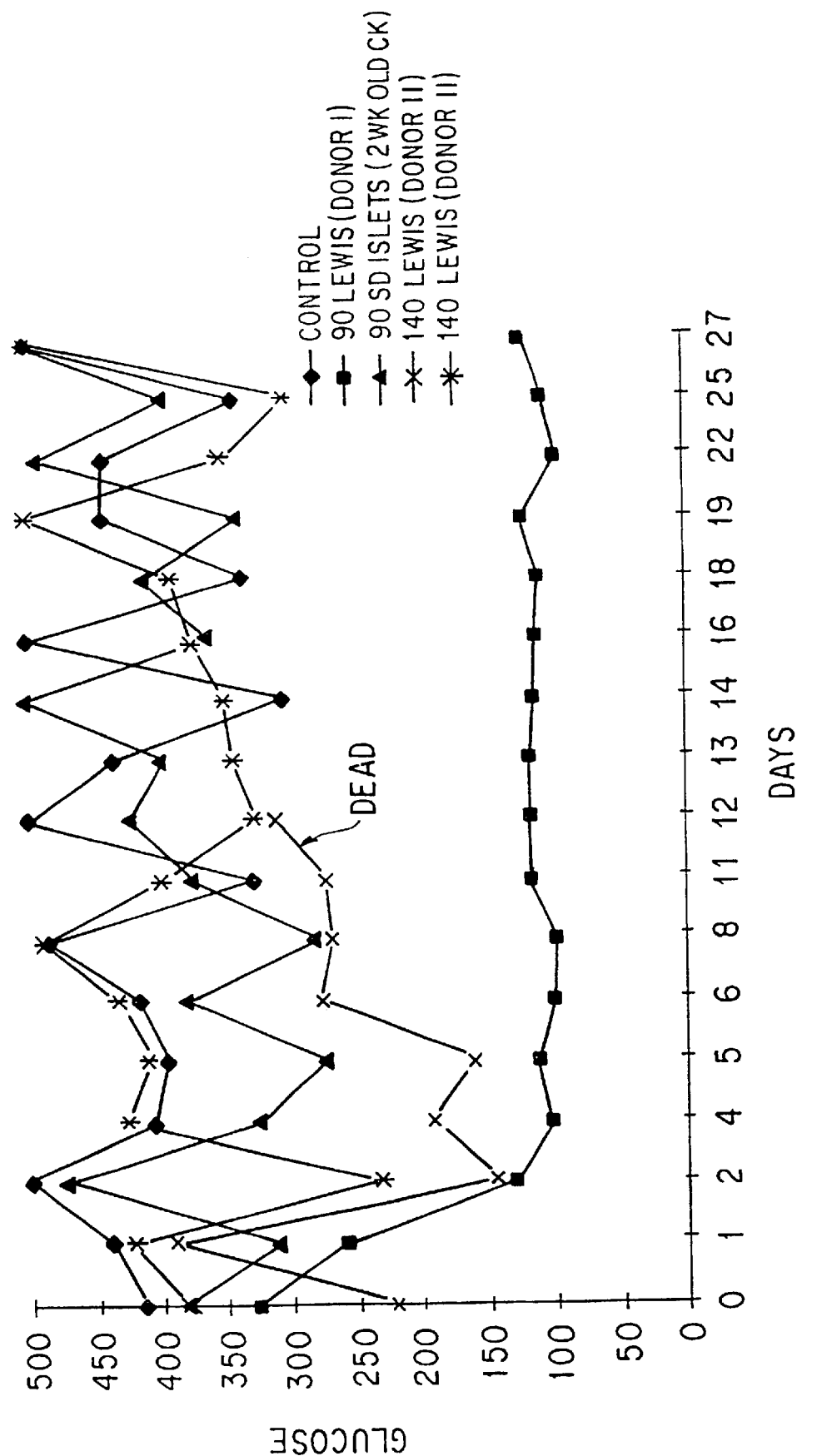
FIG. 5 shows the level of glucose through time in the presence of allogenic islet transplant.

The results are shown in FIG. 5. In rat #2, there appears to have been a functional effect of islet transplantation, producing normoglycemia for 30 days post transplant. Rat 4 also appeared to demonstrate a functional effect, but died 12 days into the experiment. Rats 2,3, and 5 did not appear to show efficacy over time. These results demonstrate the efficacy of the method of the present invention, because such an allogeneic transplant in an immunocompetent host should have been rejected totally by day 5–7 if rejection were going to occur. The fact that there was sustainable effect past day 7 is significant, particularly without any immunosuppression or preparation of the host. The lack of effect in the other animals is probably due to non-standardization of numbers of cells needed for functional effect, as is suggested by similar success rates seen in the syngeneic transplants in Experiment 4 where a titration study was performed.

Experiment 4

To determine the number of syngeneic islet cells required ind transplants to demonstrate function, the following titration experiment was performed:

| | |
|---|---|
| Rat 1 | 55 Islets |
| Rat 2 | 30 Islets |
| Rat 3 | Control |
| Rat 4 | 27 Islets |
| Rat 5 | Control 2 |
| Rat 6 | 400 Islets |
| Rat 7 | 118 Islets |
| Rat 8 | 120 Islets |
| Rat 9 | 300 Islets |

Figure 6:
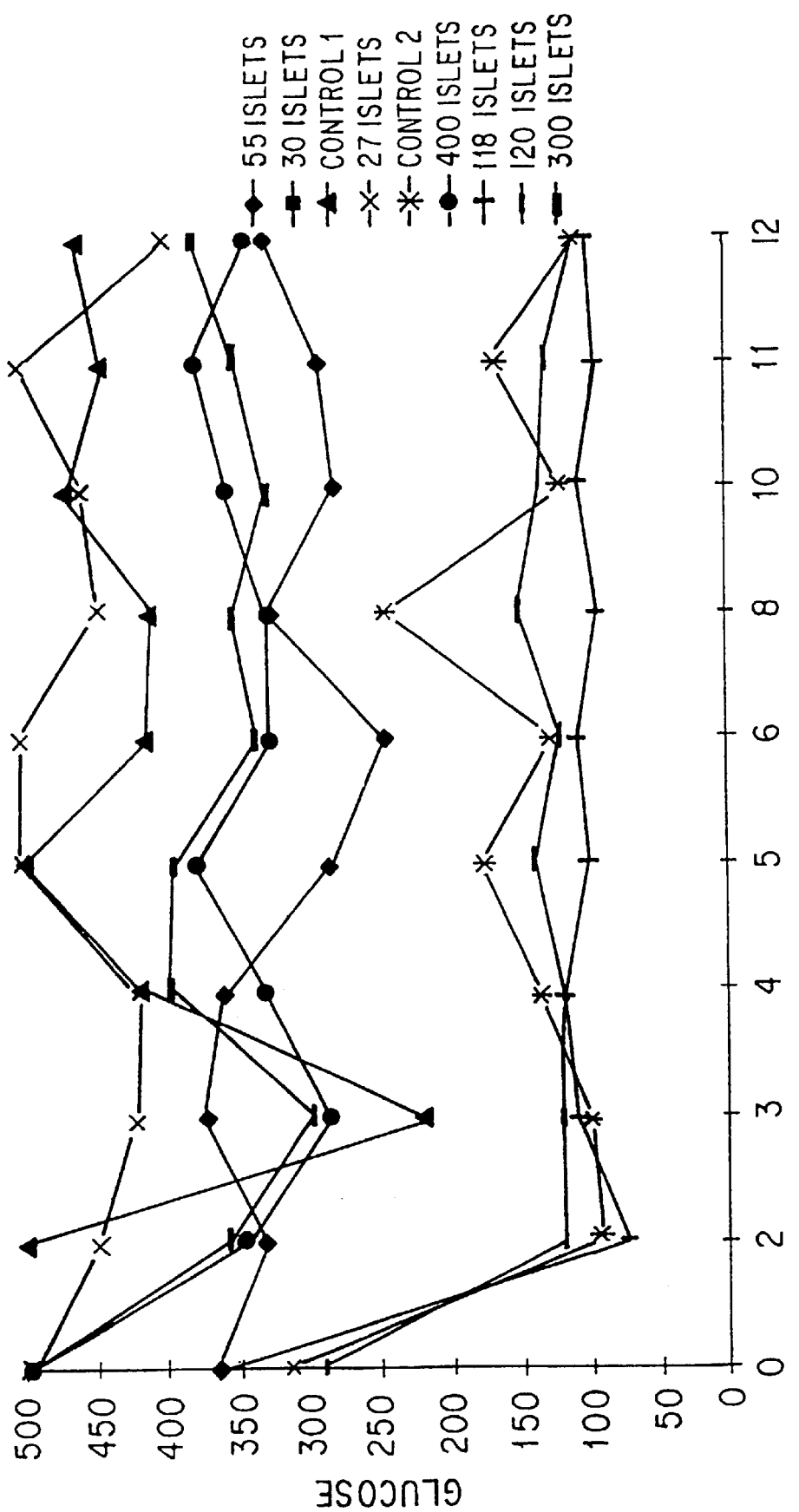
FIG. 6 shows the level of glucose through time in the presence of titrated syngeneic islet transplant.

Results are shown in FIG. 6. The results of this experiment suggest that the optimal dose is approximately 100 islets. Although not intending to be bound by theory, the fact that more islets do not appear to be functional could be due to local down-regulation that may occur due to the small volume of space present in the bone marrow space of the rat tibia.

All documents referred to herein should be considered to be incorporated by reference in their entireties.

Having generally described this invention, a further understanding can be obtained by reference to certain specific examples which are provided herein for purposes of illustration only and are not intended to be limiting unless otherwise specified.

What is claimed is:

1. A method for transplanting cells into a mammal such that the cells provoke a minimal immune response comprising delivering the cells into the bone marrow space of a bone of a mammal wherein said cells maintain at least one biological function characteristic of the transplanted cell type, wherein the cells are selected from the group consisting of hepatocytes and pancreatic islet cells.

2. A method for transplanting cells into a mammal such that the cells provoke a minimal immune response comprising delivering the cells into the bone marrow space of a bone of a mammal wherein said cells maintain at least one biological function characteristic of the transplanted cell type, wherein the cells are pancreatic islet cells and the biological function is regulation of glucose levels.

* * * * *